(12) United States Patent
Wilson

(10) Patent No.: US 9,532,793 B2
(45) Date of Patent: Jan. 3, 2017

(54) NOSE COMFORTER AND CLEANING DEVICE

(71) Applicant: Paul David Lincoln Wilson, North Port, FL (US)

(72) Inventor: Paul David Lincoln Wilson, North Port, FL (US)

( * ) Notice: Subject to any disclaimer, the term of this patent is extended or adjusted under 35 U.S.C. 154(b) by 148 days.

(21) Appl. No.: 14/338,083

(22) Filed: Jul. 22, 2014

(65) Prior Publication Data

US 2015/0039003 A1 Feb. 5, 2015

Related U.S. Application Data

(60) Provisional application No. 61/862,272, filed on Aug. 5, 2013.

(51) Int. Cl.
*A61F 9/00* (2006.01)
*A61F 11/00* (2006.01)
*A61B 17/24* (2006.01)
*A61F 13/38* (2006.01)

(52) U.S. Cl.
CPC ............... *A61B 17/24* (2013.01); *A61F 13/38* (2013.01); *A61B 2017/246* (2013.01)

(58) Field of Classification Search
CPC .... A61B 17/24; A61B 2017/246; A61F 13/38
USPC ......................................... 606/162
See application file for complete search history.

(56) References Cited

U.S. PATENT DOCUMENTS

| 6,270,510 B1 * | 8/2001 | Westendorf ............. A61F 13/38 606/162 |
| 6,923,760 B2 * | 8/2005 | Koda ..................... A61F 11/006 600/127 |
| 7,951,106 B1 * | 5/2011 | Perez .................... A61F 11/006 604/11 |

* cited by examiner

*Primary Examiner* — Katherine M Shi

(57) ABSTRACT

A disposable hygienic nostril cleansing tool is described that consists of a dual-purpose head (cotton swab and scraper tip), flexible shaft, and cotton debris cleaner in the tool body.

1 Claim, 2 Drawing Sheets

NOSE COMFORTER AND CLEANING DEVICE

FIELD OF THE INVENTION

The invention relates generally to a nostril cleansing tool.

BACKGROUND

Currently there are a number of solutions for nostril cleansing. Some of these solutions attempt to clean the inside of the nose, but these solutions fail to meet the needs of the market because the heads of the device need to be constantly cleaned and sanitized for later re-use. Other solutions attempt to remove mucous from the nostrils, but these solutions are similarly unable to meet the needs of the market because it leaves other remaining debris in the nose. Still other solutions seek to use disposable material to clean nostrils, but these solutions also fail to meet market needs because it prevents a user from cleaning nostrils multiple times with the same device before having to dispose of the cleaner.

Therefore, there currently exists a need in the market for an apparatus that is a re-usable nostril cleanser that is easy to use and hygienic and effectively clears debris from the user's nose.

SUMMARY OF THE INVENTION

It is advantageous to have an apparatus that contains a dual-purpose head that is used to clear and loosen mucous and other debris from the nose (or the ear of a user, in another embodiment). Furthermore, it is advantageous to have an apparatus for nostril cleaning device with a flexible shaft. Still further, it is advantageous to have an apparatus which cleans cotton debris. The various embodiments of the invention described herein advantageously fills the aforementioned deficiencies in the prior art by providing a disposable nostril cleaning tool which provides a dual purpose cleaning head to hygienically remove mucous and debris from a nose.

In one example embodiment, the device includes a cotton swab and scraper tip head to clean nostrils with a cavity to clean the cotton debris. The tool contains a flexible shaft for easy use, as well as a cotton debris cleaner in the cavity, which allows for the reuse of the tool. The cleaning tool can be used independently or in conjunction with a saline solution product. The flexible shaft connects the body of the device to the cotton swab and scraper tip head, which allows the user to easily loosen mucous and clear debris in the nostril. A hole or aperture is located in the middle of the tool or handle body for ergonomic gripping by the user.

In a related embodiment, the cleanser can also be used to clear earwax from a user's ear. In yet another related embodiment, the shaft of the cleanser is configured with a disc, barrier or bump stop to prevent the nose or ear cleanser from penetrating too far into the orifice to be cleaned (to prevent ear drum damage or upper nostril membrane injury).

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1:
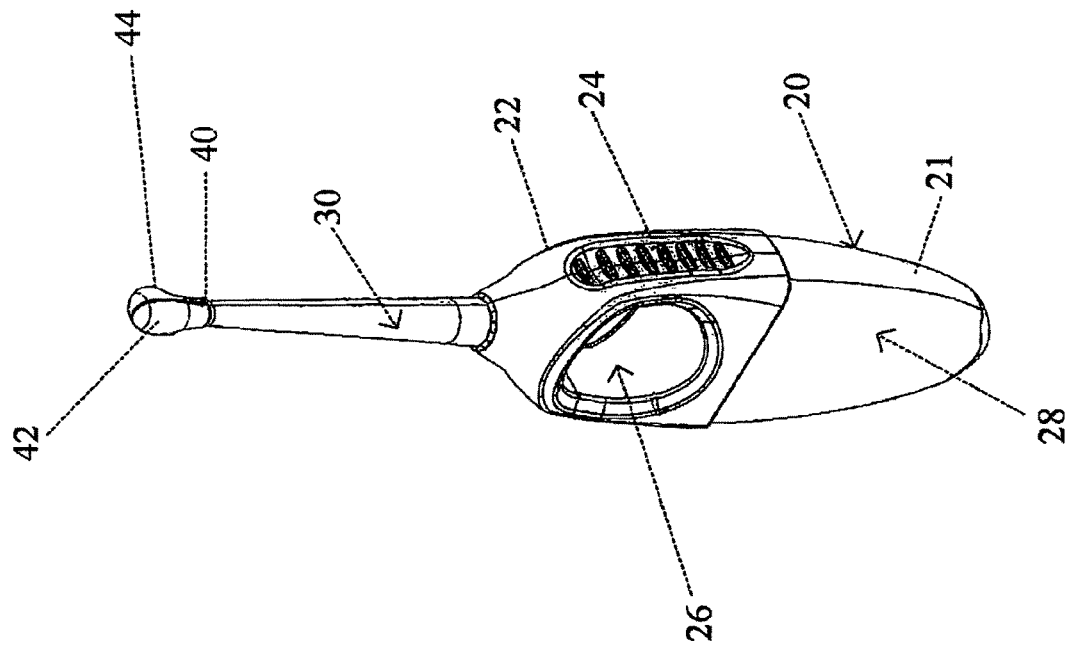
FIG. 1 illustrates a perspective view of the invention.
Figure 2:
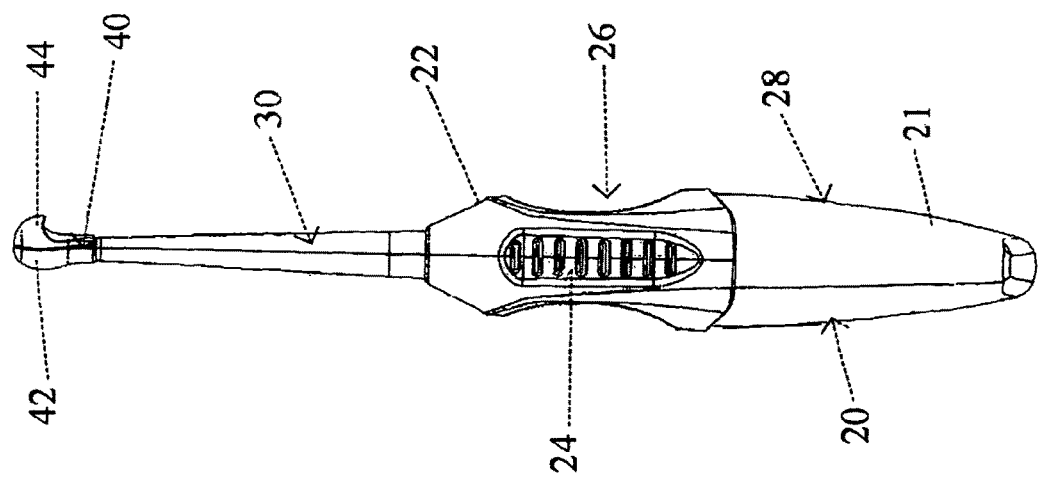
FIG. 2 illustrates a side view of the invention.

Referring to the figures, FIGS. 1-2 illustrate a perspective and side view, respectively, of a nostril cleansing device 10. In this example embodiment, nostril device 10 includes a handle assembly 20, a shaft member 30 and a cleansing head assembly 40. In this example embodiment, handle assembly 20 includes a body 21 that also serves as a cavity or cotton debris cleaner, a cap 22, grip handle 24 (located on one or both sides) an aperture 26 to accommodate the user's finger (provides an ergonomic finger grip) and a cavity/debris cleaner 28. Handle assembly 20 is coupled to a shaft member 30 that is either rigid or preferably flexible to accommodate various movements for the user. Shaft 30 has a cleansing head assembly 40 removably attached thereto comprised of a cotton swab portion 42 and a scraper tip 44. As seen in FIG. 2, the cotton swab portion 42 has a first profile, on a first radial side of the shaft member 30 and the scraper tip 44 has a second profile different than the first profile of the cotton swab, on a second radial side of the shaft member 30, wherein the second radial side is disposed opposite the first radial side.

In related example embodiments, the disposable hygienic nostril cleaning tool consists of a single-purpose head, such a cotton swab or scraper tip, or a removable cleaning head to accommodate an unused cleansing head or includes a soft sponge head for water cleaning or application of a moisturizing or antibiotic gel.

In a related embodiment, the cleanser can also be used to clear earwax from a user's ear. In yet another related embodiment, the shaft of the cleanser is configured with a disc, barrier or bump stop to prevent the nose or ear cleanser from penetrating too far into the orifice to be cleaned (to prevent ear drum damage or upper nostril membrane injury).

Various related embodiments of the invention are also described in Appendix A, which is incorporated herein by reference in its entirety. The following patents and publications are incorporated by reference in their entireties: U.S. Pat. Nos. 5,895,408 and 6,595,949 and Design Pats. D391,637 and D430,934.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. A nostril cleansing device comprising:
a handle assembly, comprising:
  a body;
  a cap, having a grip handle located on a first side or a first and second side of the handle assembly, said cap further comprising an aperture for accommodating a user's fingers to thereby provide an ergonomic finger grip;
  a cotton debris cleaner;
a shaft member having a first end, a second end and a longitudinal axis extending therethrough, wherein the shaft member is coupled to the cap of the handle assembly at the first end, wherein the shaft member is a flexible member to accommodate various movements from the user; and
a dual purpose cleansing head assembly removably attached to the shaft member on the second end of the shaft member, the dual purpose cleansing head assembly comprising a cotton swab portion with a first profile, on a first radial side of the shaft member and a scraper tip having a second profile different than the first profile of the cotton swab, on a second radial side of the shaft member, wherein the second radial side is disposed opposite the first radial side;
wherein the dual purpose cleansing head assembly is configured for loosening mucous, hygienically removing mucous and effectively clearing debris from the user's nose;
wherein a user is not prevented from cleaning nostrils of the user multiple times with the same nostril cleansing device before having to dispose of the nostril cleansing device because the nostril cleansing device can re-used without sanitizing or cleaning; and
wherein the nostril cleansing device is configured for use independently or in conjunction with a saline solution product.

* * * * *